(12) United States Patent
Weigele et al.

(10) Patent No.: US 6,420,384 B2
(45) Date of Patent: Jul. 16, 2002

(54) PROTON PUMP INHIBITORS

(75) Inventors: Manfred Weigele, Cambridge; David C. Dalgarno, Brookline; John Iuliucci, Andover; Terence P. Keenan, Cambridge; Tomi K. Sawyer, Southborough, all of MA (US)

(73) Assignee: Ariad Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/740,619

(22) Filed: Dec. 18, 2000

Related U.S. Application Data

(60) Provisional application No. 60/172,510, filed on Dec. 17, 1999, provisional application No. 60/172,161, filed on Dec. 17, 1999, and provisional application No. 60/240,788, filed on Oct. 16, 2000.

(51) Int. Cl.[7] .................. C07D 401/01; A61K 31/44
(52) U.S. Cl. ............. 514/303; 514/301; 514/341; 514/342; 514/365; 514/399; 546/114; 546/118; 546/269.7; 546/272.7; 548/186; 548/325.1
(58) Field of Search .................. 548/186, 325.1; 514/365, 399, 301, 303, 341, 342; 546/114, 118, 269.7, 272.7

(56) References Cited

U.S. PATENT DOCUMENTS

| | | | |
|---|---|---|---|
| 5,447,922 A | 9/1995 | Lawrence et al. | 514/129 |
| 5,856,314 A | 1/1999 | Kaas et al. | 514/89 |
| 5,866,556 A | 2/1999 | Oy | 514/89 |

FOREIGN PATENT DOCUMENTS

| | | |
|---|---|---|
| EP | 100718 | 10/1987 |
| EP | 279149 | 12/1992 |

OTHER PUBLICATIONS

Yamada et al., "2–[(2–Aminobenzyl)sulfinyl]–1–(2–pyridyl)–1,4,5,6–tetrahydrocyclopent[d]imidazoles as a Novel Class of Gastric H+/K+–ATPase Inhibitors" *J. Med. Chem.* 1996, 39, 596–604.
Copy of International Search Report, International Application No. PCT/US00/34502, Weigele et al., filed: Dec. 18, 2000.

*Primary Examiner*—Zinna Northington Davis
(74) *Attorney, Agent, or Firm*—Choate, Hall & Stewart; Karoline K. M. Shair

(57) ABSTRACT

Compounds and methods of treating or preventing bone disorders including osteoporosis, rheumatoid arthritis, and metastatic bone disease are provided. The inventive compounds comprise a bone targeting moiety and a payload. The payload portion of these inventive compounds inhibit the proton pump of osteoclasts, thereby reducing bone resorption. Compounds of the present invention include compounds of the following formula:

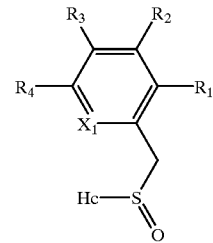

9 Claims, No Drawings

PROTON PUMP INHIBITORS

PRIORITY INFORMATION

The present application claims priority under 35 U.S.C. §119(e) to U.S. Provisional Patent Application No. 60/172,510, filed Dec. 17, 1999, entitled "Bone Targeting Agents", U.S. Provisional Patent Application No. 60,172,161, filed Dec. 17, 1999, entitled "Proton Pump Inhibbitors", and U.S. Provisional Patent Application No. 60/240,788, filed Oct. 16, 2000 entitled "Bone Targeting Agents", and the entire contents of each of these applications are hereby incorporated by reference.

BACKGROUND OF THE INVENTION

The need to treat debilitating bone disorders, such as osteoporosis, has led to extensive research on the mechanism and regulation of continuous bone formation and resorption. In particular, an appropriate balance of osteoblasts, which function to form bone tissue, and osteoclasts, which function to resorb bone tissue, is required to maintain the structural integrity and proper functioning of the skeleton in spite of continuous metabolism. Any changes in this balance of metabolism, such as an increased bone resorption (either absolute, or an increase via decreased bone formation relative to bone resorption) can lead bone diseases or disorders. One of the most common diseases resulting from this imbalance is osteoporosis, which is characterized by a decrease in bone mass and deterioration in skeletal micro-architecture leading to an increased fragility and susceptibility to fractures. Other diseases which result from alterations in bone resorption include, but are not limited to, Paget's Disease, primary and secondary hyperparathyroidism, humoral hypercalcemia of malignancy, various cancers where resorption is increased, and rheumatoid arthritis.

Because of the serious disorders that may result from a metabolic imbalance, researchers have been interested in studying bone metabolism, specifically the mechanism by which bone resorption and formation occurs, to ultimately develop a strategy for inhibiting resorption, and/or for improving bone mass and/or bone micro-architecture by stimulating osteoblast activity. However, the action of both osteoclasts and osteoblasts is controlled by a number of complex factors, and thus developing selective therapeutics has proven to be a difficult task.

One approach that has been taken for the development of novel therapeutics for bone disorders is inhibition of the osteoclast proton pump. It has been previously demonstrated that this proton pump is a vacuolar $H^+$-ATPase (see, Blair et al., *Science* 1989, 245, 855–857; Finbow et al., *Biochem. J.* 1997, 324, 697–712; Forgac, *M. Soc. Gen. Physiol. Ser.* 1996, 51, 121–132). It has been shown that osteoclasts, to effect bone resorption, ultimately lower the pH in the sealed microcompartment which underlies their site of attachment to the bone surface (see, Baron et al., *J. Cell. Biol.* 1985, 101, 2210–2222), thus resulting in the acidic envionment required to dissolve the bone mineral and to allow degradation of the bone matrix by proteases. The osteoclast uses a proton pump (an ATP-dependent transport of protons) to achieve this acidification and thus any therapeutic inhibition of the osteoclast proton pump should lead to a decrease in bone loss or turnover. As a result, many novel therapeutics developed to reduce bone resorption have focused on the inhibition of the proton pump to prevent osteoclast activity and excessive bone resorption. For a discussion of the vacuolar $H^+$-ATPase and inhibitors of vacuolar $H^+$-ATPase see Farina et al., *Exp. Opin. Ther. Patents* 1999, 9, 157–168 and David, P. and Baron, R. "The Vacuolar $H^+$-ATPase: A Potential Target for Drug Development in Bone Diseases" *Exp. Opin. Invest. Drugs* 1995, 4, 725–740.

A wide variety agents that are capable of inhibiting the action of V-ATPases have been disclosed recently. For example, it has been found that Bafilomycin $A_1$, a macrolide antibiotic, can inhibit the V-type $H^+$-ATPases at nanomolar concentrations, and thus is the most potent inhibitor of V-ATPases yet described. One major concern relating to the use of this therapeutic, as well as other derivatives representative of this family of compounds, such as concanamicin, (see, U.S. Pat. No. 5, 610, 178 "Macrolides and the Use Thereof") however, is that it is not capable of specifically inhibiting bone resorption without affecting all other V-ATPases in the body, and thus leads to systemic alteration of cellular physiology and high toxicity. Other therapeutics, such as N-ethylmaleimide, have also proven to be effective inhibitors of V-ATPases, however there is also the concern that these agents may affect other V-type $H^+$-ATPases in vivo. Additionally, gallium and group III metals, nitrate, vanadate, omeprazole and related compounds, WY 47766, S238, and bisphopshonates have also demonstrated inhibition of the osteoclast proton pump, although less effectively or with adverse side effects (see, Baron et al. *Exp. Opin. Invest. Drugs* 1995, 4, 725 and Farina et al. *Exp. Opin. Ther. Patents* 1999, 9, 157–168).

Clearly, although progress has been made towards developing therapeutic agents for osteoporosis and other bone disorders, there remains a need to develop potent and selective agents having minimal side effects. In particular, there remains a need to develop selective inhibitors of the osteoclast proton pump.

SUMMARY OF THE INVENTION

The present invention provides compounds comprising a bone targeting moiety and a payload and methods for the prevention and/or treatment of bone disorders and/or other related conditions using these compounds or pharmaceutical compositions thereof. In general, the compounds of the present invention comprise a bone targeting moiety and a payload capable of effecting inhibition of the osteoclast proton pump.

Thus, in one aspect, the present invention provides compounds of Formula (I):

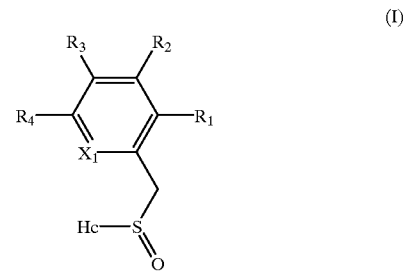

(I)

wherein $X_1$ is CH or N;

wherein $R_1$, $R_2$, $R_3$, and $R_4$ are each independently hydrogen, lower alkyl, halogen, hydroxy, alkyloxy, aryl, aryloxy, heteroaryl, trifluoromethoxy, cyano, nitro, thio, alkylthio or a bone targeting moiety, wherein said bone targeting moiety is selected from any one of i-xx:

i
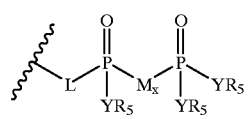
ii
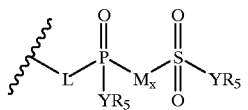
iii
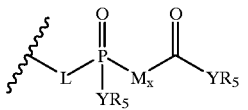
iv
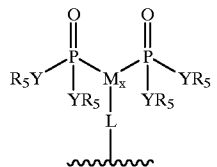
v
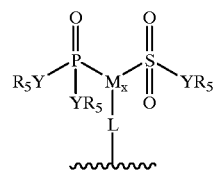
vi
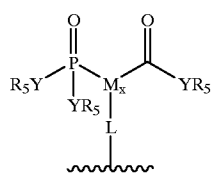
vii
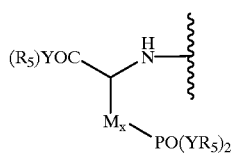
viii
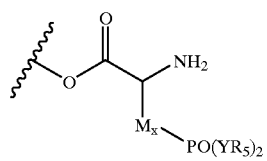
ix
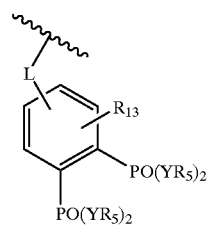
x
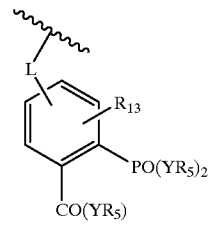
xi
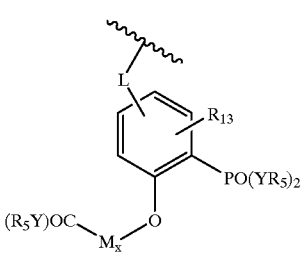
xii
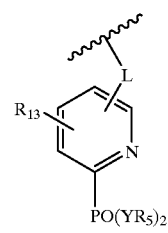
xiii
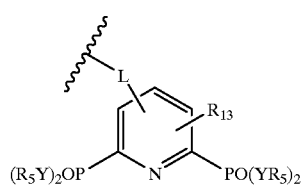
xiv
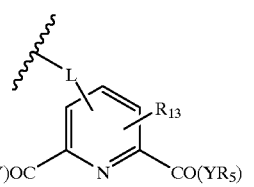
xv
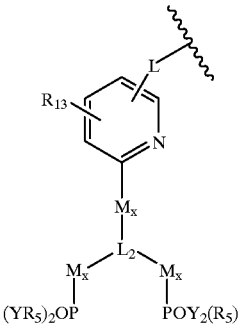

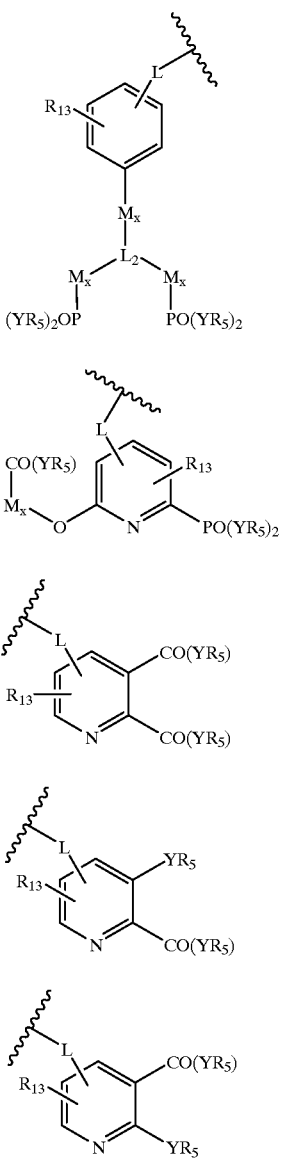

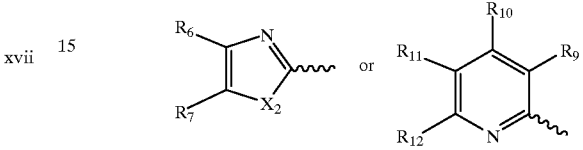

wherein each occurrence of M is independently CV$_2$, —NV—, —O— or —S—, wherein each occurence of V is independently hydrogen, OH, halogen, or aliphatic; each occurrence of Y is independently a covalent bond, —O—, —S— or N(R$_j$)$_2$, wherein R$_j$, for each occurrence, is is independently hydrogen, aliphatic, heteroaliphatic, aryl, heteroaryl, alkylaryl, or alkylheteroaryl; each occurrence of x is independently 0–6, and for compounds i-vi, xi, and xvii, x may preferably be 1–6; wherein L is —(Ch$_2$)$_p$—He—(CH$_2$)$_n$—, wherein He is absent or is NR', O or S, wherein R' is hydrogen or lower alkyl, n is 0–5, and p is 0–5, except when He is absent, the sum of n and p is 1–5; wherein L$_2$ is N or CR$_K$, wherein R$_K$ is hydrogen, aliphatic, heteroaliphatic, aryl, heteroaryl, alkylaryl, or alkylheteroaryl; and wherein each occurrence of R$_5$ is independently hydrogen or lower alkyl, with the proviso that if either of R$_2$ or R$_4$ are bone targeting moieties, He, for the bone targeting moiety at R$_2$ or R$_4$, is NR', O, or S, wherein R' is hydrogen or lower alkyl; wherein R$_{13}$ represents 0–3 substituents selected from hydrogen, halogen, lower alkyl, lower alkenyl, aryl, heteroaryl, carbonyl, thiocarbonyl, ketone, aldehyde, amino, acylamino, amido, amidino, cyano, nitro, azido, sulfonyl, sulfoxido, sulfate, sulfonate, sulfamoyl, sulfonamido, phosphoryl, phosphorothioate, phosphonate, phosphinate, —(CH$_2$)$_t$-alkyl-, —(CH$_2$)$_t$-alkenyl-, (CH$_2$)$_t$ alkynyl-, —(CH$_2$)$_t$aryl-, —(CH$_2$)$_t$aralkyl-, —(CH$_2$)$_t$OH—, —(CH$_2$)$_t$O-lower alkyl-, (CH$_2$)$_t$)-lower alkenyl, —O(CH$_2$)$_t$ R, —(CH$_2$)$_t$S-lower alkyl, —(CH$_2$)$_t$S-lower alkenyl, —S(CH$_2$)$_t$R, —(CH$_2$)$_t$NR$_2$, (CH$_2$)$_t$NR-lower alkyl, —(CH$_2$)$_t$NR-lower alkenyl, —NR(CH$_2$)$_t$R, or protected forms of the above, and wherein t is 1–10;

wherein Hc is:

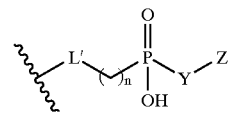

wherein R$_6$, R$_7$, R$_9$, R$_{10}$, R$_{11}$, and R$_{12}$ are each independently selected from the group consisting of bone targeting moiety as described above, hydrogen, lower alkyl, substituted or unsubstituted aryl, and substituted or unsubstituted heteroaryl; or wherein R$_6$ and R$_7$ taken together, or any one of R$_{11}$ and R$_{12}$, R$_{10}$ and R$_{11}$, and R$_9$ and R$_{10}$ taken together, comprise a substituted or unsubstituted aryl, heteroaryl, or cycloalkyl moiety, wherein said substituted or unsubstituted aryl, heteroaryl, or cycloalkyl moiety is a single ring or is polycyclic; and wherein wherein X$_2$ comprises NR$_8$ or S, wherein R$_8$ is hydrogen, lower alkyl, substituted or unsubstitued aryl, or substituted or unsubstituted heteroaryl; and whereby at least one of R$_1$–R$_4$ or R$_6$, R$_7$, R$_9$–R$_{12}$ is substituted with a bone targeting moiety as described above.

In certain embodiments of the compounds as described above, at least one occurrence of Y is O. In certain other embodiments of the compounds as described above, each occurrence of Y is O.

In certain embodiments for compounds as described above, R$_6$ and R$_7$ taken together comprise a substituted or unsubstituted aryl, heteroaryl, or cycloalkyl moiety, and said aryl, heteroaryl, or cycloalkyl moiety is a substituted single or polycyclic ring. In certain other embodiments, substituted single or polycyclic ring is substituted with methyl or alkoxy.

In other embodiments, the present invention provides compounds as described above, wherein the bone targeting moiety comprises a structure of formula (II)

(II)

$$\text{L'}-(CH_2)_n-\overset{\overset{O}{\|}}{\underset{\underset{OH}{|}}{P}}-Y-Z$$

wherein n is 0–5; wherein L' is —(CH$_2$)$_p$—He—, and He is absent or is NR', O, or S, wherein R' is hydrogen or lower alkyl, and p is 0–5, except when He is absent, the sum of n and p is 1–5, with the proviso that if either of R$_2$ or R$_4$ are bone targeting moieties, He, for the bone targeting moiety for R$_2$ or R$_4$, is NR', O, or S, wherein R' is hydrogen or lower alkyl; wherein Y is (CH$_2$)$_q$, wherein q is 1–3, or NH; and wherein Z is PO(OR$_{14}$)$_2$, SO$_2$(OR$_{14}$), or COOR$_{14}$, wherein each occurence of R$_{14}$ is independently hydrogen or lower alkyl.

In still other embodiments, R$_1$, R$_3$ and R$_4$ are each hydrogen; R$_2$ is a bone targeting moiety of formula (II); p is O and He is either NR', wherein R' is hydrogen or lower alkyl, or O; wherein He is

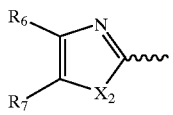

wherein $X_2$ is NH, and $R_6$ and $R_7$ taken together comprise a pyridyl group; wherein Y is $CH_2$ or NH; wherein Z is $PO(OR_{14})_2$; and wherein $R_{14}$ is hydrogen or lower alkyl.

In certain other embodiments, $R_1$ and $R_3$ are each hydrogen; wherein $R_4$ is alkoxy; $R_4$ is alkoxy; $R_2$ is a bone targeting group of formula (II); p is O and He is NR', wherein R' is hydrogen or lower alkyl, or O; wherein $X_1$ is CH; wherein He is

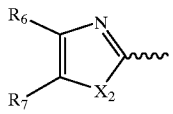

wherein $X_2$ is NH; and $R_6$ and $R_7$ taken together comprise a pyridyl group; wherein Y is $CH_2$ or NH; and wherein Z is $PO(OR_{14})_2$, and $R_{14}$ is hydrogen or lower alkyl.

In still other embodiments, $R_1$ and $R_3$ are each independently a lower alkyl or hydrogen; $R_4$ is hydrogen; $R_2$ is bone targeting moiety of formula (II); p is O and He is NR', wherein R'is hydrogen or lower alkyl, or O; wherein $X_1$ is N; wherein Hc is

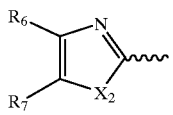

wherein $X_2$ is NH; wherein $R_6$ and $R_7$ taken together comprises a substituted or unsubstituted phenyl group; wherein Y is $CH_2$ or NH; and wherein Z is $PO(OR_{14})_2$, and $R_{14}$ is hydrogen or lower alkyl. In certain embodiments said phenyl group is substituted with an electron donating moiety.

In another aspect, the present invention provides pharmaceutical compositions comprising any one of the compounds of the present invention and a pharmceutically acceptable carrier or excipient.

In yet another aspect, the present invention provides a method for the treatment and/or prophylaxis of a disease or secondary condition associated with overactivity of osteoclasts in mammals which method comprises the administration of an effective non-toxic amount of a selective inhibitor of mammalian osteoclasts to a patient in need. In certain preferred embodiments, this selective inhibitor of mammalian osteoclasts inhibits the osteoclast proton pump mechanism. While the treatment of any disease or condition associated with the overactivity of osteoclasts is contemplated by the method of the present invention, it is preferred that the disease or secondary condition is selected from the group consisting of osteoporosis, Paget's Disease, hypercalcemia, rheumatoid arthritis, cancer, metastatic bone destruction, and immune disorder.

Definitions

As mentioned above, this invention provides a novel class of bone targeted compounds useful for the treatment and/or prevention of metabolic bone disorders, preferably by inhibition of bone resorption, and more preferably by inhibition of bone resorption resulting from inhibition of the osteoclast proton pump. Compounds of this invention comprise those of Formula I, set forth herein, and are illustrated in part by the various classes, subgenera and subsets of compounds described above, and by the various subgenera and species disclosed elsewhere in the specification, claims and figures. It will be appreciated that the inventive compounds may be in the form of an individual enantiomer, diastereomer or geometric isomer, or may be in the form of a mixture of stereoisomers.

Also included are pharmaceutically acceptable derivatives of the foregoing compounds, where the phrase "pharmaceutically acceptable derivative" denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof, preferably one which is capable of inhibiting bone resorption. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. One technique for providing a prodrug of a compound of the present invention is described generally in Niemi et al., *J. Med. Chem.* 1999, 42, 5053–5058.

The term "inhibition of bone resorption" or "bone resorption inhibiting", as used herein, means treating or preventing bone resorption by the direct or indirect alteration of osteoclast function or activity. Inhibition of bone resorption refers to treatment or prevention of bone loss, especially the inhibition of removal of existing bone either from the mineral phase and/or the organic matrix phase, through direct or indirect alteration of osteoclast formation or activity. In preferred embodiments, the inhibition of bone resorption is achieved by inhibition of the osteoclast proton pump.

Any of a variety of in vivo or in vitro assays may be employed to assess the ability of inventive compositions to inhibit bones resorption and/or proton pump activity (see, for example, the Exemplification section, which describes a useful rabbit osteoclast assay). In particularly preferred embodiments of the invention, the observed inhibition of bones resorption and/or proton pump activity is selective in that the inventive compositions do not exert significant negative effects on biological processes other than bone resorption. For example, particularly preferred inventive compositive show specific inhibition of the osteoclast proton pump as compared with other proton pumps. In some cases, such specific inhibition may result from specific localization of the inventive composition to osteoclasts, so that compositions delivered in vivo do not have the opportunity to inhibit other proton pumps; in other cases, specific inhibition may be attributed to specific action of the inventive payload on the osteoclast proton pump as compared with other proton pumps.

The term "payload," in general, includes therapeutic agents (e.g., a small molecule, a drug, a radiotherapeutic atom, etc.), detectable labels (e.g., fluorescent, radioactive, radiopaque, etc.), or any other moiety desired to be delivered to the site of an abnormal condition. In the context of the present invention, particularly preferred payloads include those capable of acting as inhibitors of the osteoclast proton pump.

"Subject" shall mean a human or animal (e.g., rat, mouse, cow, pig, horse, sheep, monkey, cat, dog, goat etc.).

A "target" shall mean an in vivo site to which targeted agents bind. A target may refer to a molecular structure to which a targeting moiety binds, such as a hapten, epitope, receptor, dsDNA fragment, carbohydrate, or enzyme. Alternatively or additionally, a target may be a type of tissue, e.g., bone. A preferred target is bone. In certain preferred embodiments of the present invention, target cells include osteoclasts.

The term "targeting moiety" refers to any molecular structure which assists the inventive composite in localizing to a particular target area, entering a target cell(s), and/or binding to a target receptor. As described herein, the compounds of the present invention are targeted to bone, and more preferably are osteoclast selective.

A "therapeutic agent" shall mean an agent capable of having a biological effect on a host. Preferred therapeutic agents are capable of preventing or reducing one or more symptoms of a metabolic disorder resulting from overactivity of ostecoclasts. In a preferred embodiment for treating osteoporosis, the therapeutic agent is an inhibitor of the osteoclast proton pump.

A named R group will generally have the structure which is recognized in the art as corresponding to R groups having that name. For the purposes of illustration, representative R groups as enumerated in the specification and claims of the present application are defined herein. These definitions are intended to supplement and illustrate, not preclude, the definitions known to those of skill in the art.

The term "independently selected" is used herein to indicate that the R groups can be identical or different.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphorothioate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphorothioate, phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group). Exemplary aralkyl groups include, but are not limited to, benzyl and more generally $(CH_2)_n Ph$, where Ph is phenyl or substituted phenyl, and n is 1, 2, or 3.

The terms "alkenyl" and "alkynyl" refer to unsaturated aliphatic groups analogous in length and possible substitution to the alkyls described above, but that contain at least one double or triple bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

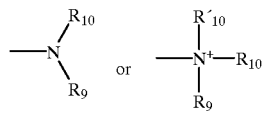

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

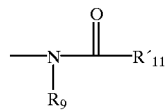

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

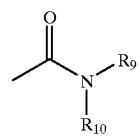

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

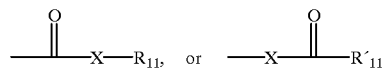

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfir, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

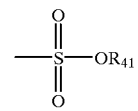

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in this list, and all abbreviations utilized by organic chemists of ordinary skill in the art are hereby incorporated by reference.

The term "sulfate" is art recognized and includes a moiety that can be represented by the general formula:

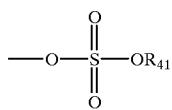

in which $R_{41}$ is as defined above.

The term "sulfonamido" is art recognized and includes a moiety that can be represented by the general formula:

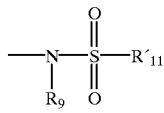

in which $R_9$ and $R'_{11}$ are as defined above.

The term "sulfamoyl" is art-recognized and includes a moiety that can be represented by the general formula:

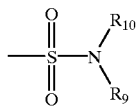

in which $R_9$ and $R_{10}$ are as defined above.

The term "sulfonyl", as used herein, refers to a moiety that can be represented by the general formula:

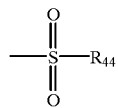

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

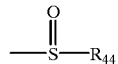

in which $R_{44}$ is selected from the group consisting of hydrogen, alky, alkenyl, alkynyl, cycloalkyl, heterocyclyl, aralkyl, or aryl.

A "phosphoryl" can in general be represented by the formula:

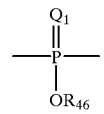

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

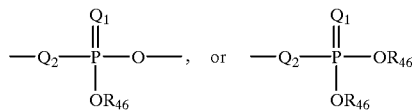

wherein $Q_1$ represents S or O, and each R46 independently represents hydrogen, a lower alkyl or an aryl, $Q_2$ represents O, S or N. When Q is an S, the moiety is a "phosphorothioate".

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2$^{nd}$* ed.; Wiley: New York, 1991, incorporated herein by reference).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., bone targeting agents), wherein one or more simple variations of substituents are made which do not adversely affect the efficacy of the compound in targeting bone. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover.

DETAILED DESCRIPTION OF CERTAIN PREFERRED EMBODIMENTS OF THE INVENTION

As discussed above, there remains a need to develop selective and potent agents for treatment and/or prevention of bone disorders, and in particular, as specific inhibitors of the osteoclast proton pump.

Thus, in general, the present invention provides compounds comprising a bone targeting agent and a payload for use in the treatment and/or prevention of bone and other related disorders. In certain embodiments, these compounds and compositions are used to treat disorders resulting from overactive osteoclast function. In certain preferred embodiments, the compounds and compositions are used to inhibit the osteoclast proton pump. In certain other preferred embodiments, these compounds and compositions are used to treat osteoporosis and other related bone metabolic disorders.

Compounds of the Invention

The present invention provides compounds, pharmaceutical compositions and methods of selective treatment and/or prevention of bone disorders. In certain embodiments, these compounds and compositions are used to treat disorders resulting from overactive osteoclast function. In certain preferred embodiments, these compounds and compositions are selective inhibitors of the osteoclast proton pump. In general, the compounds of the present invention comprise a therapeutic payload capable of inhibition of the osteoclast proton pump and a bone targeting moiety capable of targeting the therapeutic agent to bone selectively.

In one aspect, the present invention provides compounds of Formula (I):

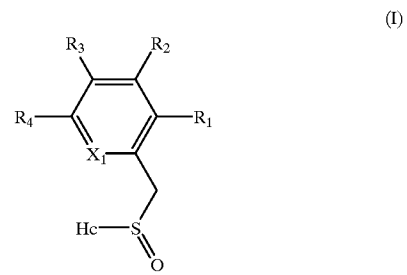

wherein $X_1$ is CH or N;

wherein $R_1$, $R_2$, $R_3$, and $R_4$ are each independently hydrogen, lower alkyl, halogen, hydroxy, alkyloxy, aryl, aryloxy, heteroaryl, trifluoromethoxy, cyano, nitro, thio, alkylthio or a bone targeting moiety, wherein said bone targeting moiety is selected from any one of i-xx:

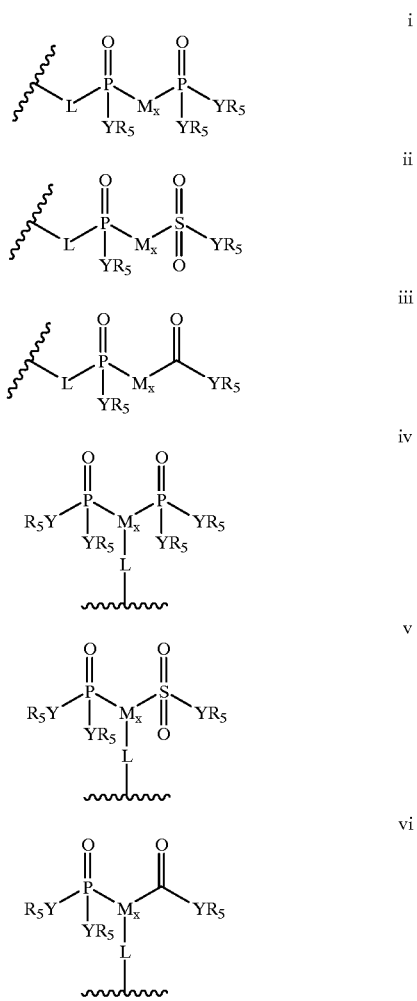

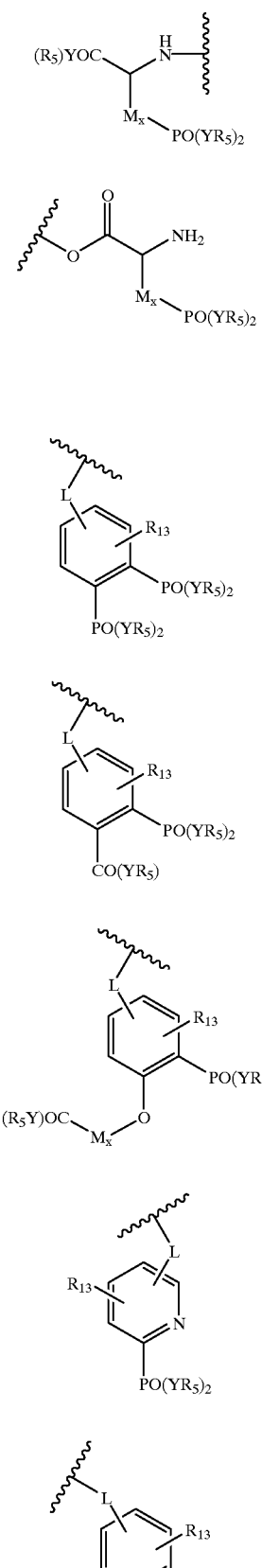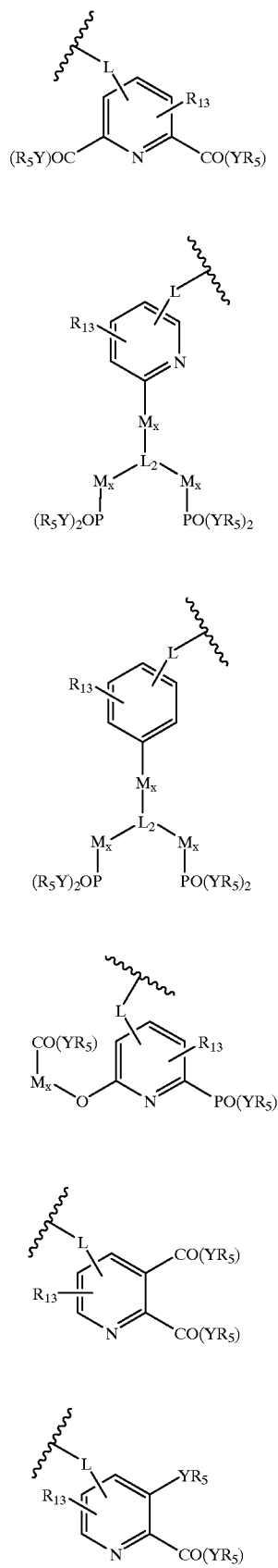

-continued

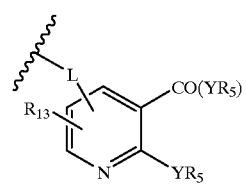

wherein each occurrence of M is independently $CV_2$, —NV—, —O— or —S—, wherein each occurrence of V is independently hydrogen, OH, halogen, or aliphatic; each occurrence of Y is independently a covalent bond, —O—, —S— or $N(R_j)_2$, wherein $R_j$, for each occurrence, is independently hydrogen, aliphatic, heteroaliphatic, aryl, heteroaryl, alkylaryl, or alkylheteroaryl; each occurrence of x is independently 0–6, and for compounds i-vi, xi, and xvii, x may preferably be 1–6; wherein L is —$(CH_2)_p$—He—$(CH_2)_n$—, wherein He is absent or is NR', O or S, wherein R' is hydrogen or lower alkyl, n is 0–5, except when He is absent, the sum of n and p is 1–5; wherein $L_2$ is N or $CR_K$, wherein $R_K$ is hydrogen, aliphatic, heteroaliphatic, aryl, heteroaryl, alkylaryl, or alkylheteroaryl; and wherein each occurrence of $R_5$ is independently hydrogen or lower alkyl, with the proviso that if either of $R_2$ or $R_4$ are bone targeting moieties, He, for the bone targeting moiety at $R_2$ or $R_4$, is NR', O or S, wherein R' is hydrogen or lower alkyl; wherein $R_{13}$ represents 0–3 substitutents selected from hydrogen, halogen, lower alkyl, lower alkenyl, aryl, heteroaryl, carbonyl, thiocarbonyl, ketone, aldehyde, amino, acylamino, amido, amidino, cyano, nitro, azido, sulfonyl, sulfoxido, sulfate, sulfonate, sulfamoyl, sulfonamido, phosphoryl, phosphorothioate, phosphonate, phosphinate, —$(CH_2)_t$-alkyl-, —$(CH_2)_t$-alkenyl-, $(CH_2)_t$aklynyl-, —$(CH_2)_t$aryl-, —$(CH_2)_t$aralkyl-, —$(CH_2)_t$OH—, —$(CH_2)_t$O-lower alkyl-, $(CH_2)_t$)-lower alkenyl, —$O(CH_2)_tR$, —$(CH_2)_t$S-lower alkyl, —$(CH_2)_t$S-lower alkenyl, —$S(CH_2)_tR$, —$(CH_2)_tNR_2$, —$(CH_2)_t$NR-lower alkyl, —$(CH_2)_t$NR-lower alkenyl, —NR $(CH_2)_tR$, or protected forms of the above, and wherein t is 1–10;

wherein Hc is:

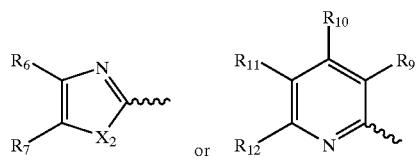

wherein $R_6$, $R_7$, $R_9$, $R_{10}$, $R_{11}$, and $R_{12}$ are each independently selected from the group consisting of bone targeting moiety as described above, hydrogen, lower alkyl, substituted or unsubstituted aryl, and substituted or unsubstituted heteroaryl; or wherein $R_6$ and $R_7$ taken together, or any one of $R_{11}$ and $R_{12}$, $R_{10}$ and $R_{11}$, and $R_9$ and $R_{10}$ taken together, comprise a substituted or unsubstituted aryl, heteroryl, or cycloalkyl moiety, wherein said substituted or unsubstituted aryl, heteroaryl, or cycloalkyl moiety is a single ring or is polycyclic; and wherein wherein $X_2$ comprises $NR_8$ or S, wherein $R_8$ is hydrogen, lower alkyl, substituted or unsubstitued aryl, or substituted or unsubstituted heteroaryl; and whereby at least one of $R_1$–$R_4$ or $R_6$, $R_7$, $R_9$–$R_{12}$ are substituted with a bone targeting moiety as described above.

In certain embodiments for compounds as described above, $R_6$ and $R_7$ taken together comprise a substituted or unsubstituted aryl, heteroryl, or cycloalkyl moiety, and said aryl, heteroaryl, or cycloalkyl moiety is a substituted single or polycyclic ring. In certain other embodiments, substituted single or polycyclic ring is substituted with methyl or alkoxy.

In other embodiments, the present invention provides compounds as described above, wherein the bone targeting moiety comprises a structure of formula (II)

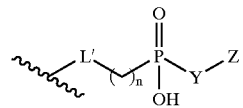

wherein n is 0–5; wherein L' is —$(CH_2)_p$—He—, and He is absent or is NR', O, or S, wherein R' is hydrogen or lower alkyl, and p is 0–5, except when He is absent, the sum of n and p is 1–5, with the proviso that if either of $R_2$ or $R_4$ are bone targeting moieties, He, for the bone targeting moiety for $R_2$ or $R_4$, is NR', O, or S, wherein R' is hydrogen or lower alkyl; wherein Y is $(CH_2)_q$, wherein q is 1–3, or NH; and wherein Z is $PO(OR_{14})_2$, $SO_2(or_{14})$, or $COOR_{14}$, wherein each occurrence of $R_{14}$ is independently hydrogen or lower alkyl.

In still other embodiments, $R_1$, $R_3$ and $R_4$ are each hydrogen; $R_2$ is a bone targeting moiety of formula (II); p is 0 and He is either Nr', wherein R' is hydrogen or lower alkyl, or O; wherein He is

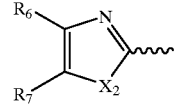

wherein $X_2$ is NH, and $R_6$ and $R_7$ taken together comprise a pyridyl group; wherein Y is $CH_2$ or NH; wherein Z is $PO(OR_{14})_2$; and wherein $R_{14}$ is hydrogen or lower alkyl.

In certain other embodiments, $R_1$ and $R_3$ are each hydrogen; wherein $R_4$ is alkoxy; $R_2$ is a bone targeting group of formula (II); p is 0 and He is NR', wherein R' is hydrogen or lower alkyl, or O; wherein $X_1$ is CH; wherein Hc is

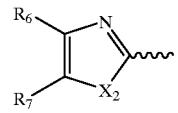

wherein $X_2$ is NH; and $R_6$ and $R_7$ taken together comprises a pyridyl group; wherein Y is $CH_2$ or NH; and wherein Z is $PO(OR_{14})_2$, and $R_{14}$ is hydrogen or lower allkyl.

In still other embodiments, $R_1$ and $R_3$ are each independently a lower alkyl or hydrogen; $R_4$ is hydrogen; $R_2$ is bone targeting moiety of formula (II); p is 0 and He is NR', wherein R' is hydrogen or lower alkyl, or O; wherein $X_1$ is N; wherein Hc is

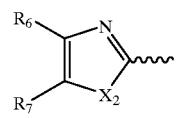

wherein $X_2$ is NH; wherein $R_6$ and $R_7$ taken togehter comprise a substituted or unsubstituted phenyl group;

wherein Y is $CH_2$ or NH; and wherein Z is $PO(OR_{14})_2$, and $R_{14}$ is hydrogen or lower alky. In certain embodiments said phenyl group is substituted with an electron donating moiety.

While not wishing to be bound by any particular theory, it is believed that the compounds of the present invention inhibit the osteoclast proton pump (via inactivation of $H^+/K^+$-ATPase) via the mechanism as shown in Scheme 1 (as demonstrated for omeprazole, an inhibitor of gastric H+/K+ ATPase; see, Yamada et al., *J. Med. Chem.* 1996, 39, 596–604 and references cited therein). In general, it is believed that in the presence of acid, (1) is transformed into the sulfenic acid (2) and the cyclic sulfenamide (3), both of which are able to react rapidly with thiol groups on the enzyme to form a complex (4) with a tightly bound disulfide bond.

Although other modes of action may be contemplated for the inventive compounds, in certain preferred embodiments, the compounds of the present invention are capable of inhibiting the ostecoclast proton pump in a similar fashion. The inventive compounds thus contemplate the incorporation of the bone targeting moieties to achieve selectivity while still retaining the desired potent mode of action for inhibition of the osteoclast proton pump.

Solid Phase Synthesis and Combinatorial Libraries of Proton Pump Inhibitors

It will be appreciated that, in addition to preparing the inventive compounds using traditional solution phase techniques, the present invention contemplates the preparation of compounds and libraries of compounds using solid phase techniques. Thus, the desired components may be modified so that they may be attached to the solid support. The use of a solid support bound component enables the use of more rapid split and pool techniques to generate larger libraries (e.g., greater than 10,000 members) more easily. It will be appreciated that solid phase parallel synthesis techniques also can be utilized, such as those described in U.S. Pat. Nos. 5,712,171 and 5,736,412.

A solid support, for the purposes of this invention, is defined as an insoluble material to which compounds are attached during a synthesis sequence. The use of a solid support is advantageous for the synthesis of libraries because the isolation of support-bound reaction products can be accomplished simply by washing away reagents from the support-bound material and therefore the reaction can be driven to completion by the use of excess reagents. Additionally, the use of a solid support also enables the use of specific encoding techniques to "track" the identity of the

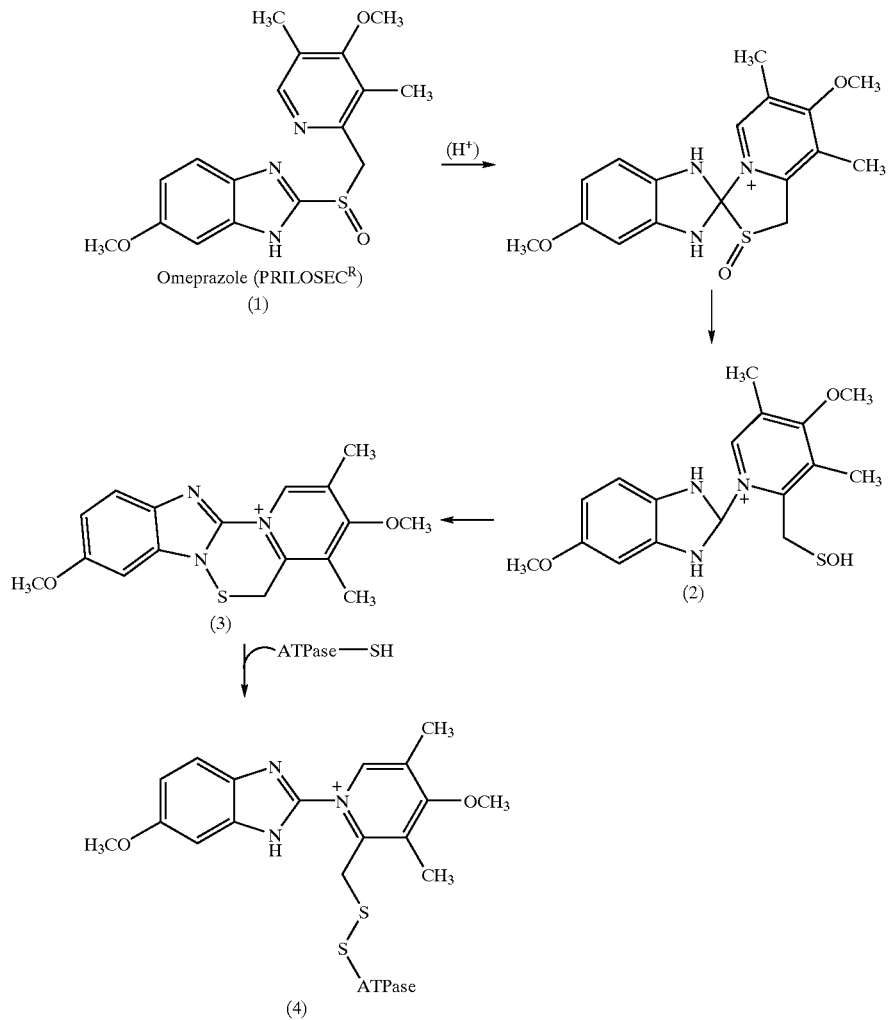

Scheme 1 inventive compounds in the library. A solid support can be any material which is an insoluble matrix and can have a rigid or semi-rigid surface. Exemplary solid supports include, but are not limited to, pellets, disks, capillaries, hollow fibers, needles, pins, solid fibers, cellulose beads, pore-glass beads, silica gels, polystyrene beads optionally cross-linked with divinylbenzene, grafted co-poly beads, poly-acrylamide beads, latex beads, dimethylacrylamide beads optionally crosslinked with N-N'-bis-acryloylethylenediamine, and glass particles coated with a hydrophobic polymer. One of ordinary skill in the art will realize that the choice of particular solid support will be limited by the compatability of the support with the reaction chemistry being utilized. An exemplary solid support is a Tentagel amino resin, a composite of 1) a polystyrene bead crosslinked with divinylbenzene and 2) PEG (polyethylene glycol), is employed for use in the present invention. Tentagel is a particularly useful solid support because it provides a versatile support for use in on-bead or off-bead assays, and it also undergoes excellent swelling in solvents ranging from toluene to water.

Specific compounds may be attached directly to the solid support or may be attached to the solid support through a linking reagent. Direct attachment to the solid support may be useful if it is desired not to detach the library member from the solid support. For example, for direct on-bead analysis of biological/pharmacological activity or analysis of the compound structure, a stronger interaction between the library member and the solid support may be desirable. Alternatively, the use of a linking reagent may be useful if more facile cleavage of the inventive library members from the solid support is desired.

Furthermore, any linking reagent used in the present invention may comprise a single linking molecule, or alternatively may comprise a linking molecule and one or more spacer molecules. A spacer molecule is particularly useful when the particular reaction conditions require that the linking molecule be separated from the library member, or if additional distance between the solid support/linking unit and the library member is desired. In one particularly preferred embodiment, photocleavable linkers are employed to attach the solid phase resin to the component. Photocleavable linkers are advantageous because of the ability to use these linkers in in vivo screening strategies. Once the compound is released from the solid support via photocleavage, the compound is able to enter the cell. Exemplary photocleavable linkers include, but are not limited to ortho-Nitrobenzyl photolinkers and dithiane protected benzoin photolinkers. One of ordinary skill in the art will realize that the method of the present invention is not limited to the use of photocleavable linkers; rather other linkers may be employed, preferably those that are capable of delivering the desired compounds in vivo.

Thus, the synthesis of libraries of osteoclast proton pump inhibitors can be performed using established combinatorial methods for solution phase, solid phase, or a combination of solution phase and solid phase synthesis techniques. The synthesis of combinatorial libraries is well known in the art and has been reviewed (see, e.g., "Combinatorial Chemistry", Chemical and Engineering News, Feb. 24, 1997, p. 43; Thompson, L. A., Ellman, J. A., *Chem. Rev.* 1996, 96, 555, incorporated herein by reference.) One of ordinary skill in the art will realize that the choice of method will depend upon the specific number of compounds to be synthesized, the specific reaction chemistry, and the availability of specific instrumentation, such as robotic instrumentation for the preparation and analysis of the inventive libraries. In particularly preferred embodiments, the reactions to be performed on the inventive scaffolds to generate the libraries are selected for their ability to proceed in high yield, and in a stereoselective fashion, if applicable.

In one embodiment of the present invention, libraries are generated using a solution phase technique. Traditional advantages of solution phase techniques for the synthesis of combinatorial libraries include the availability of a much wider range of organic reactions, and the relative ease with which products can be characterized. In a preferred embodiment, for the generation of a solution phase combinatorial library, a parallel synthesis technique is utilized, in which all of the products are assembled separately in their own reaction vessels. In a particularly preferred parallel synthesis procedure, a microtitre plate containing n rows and m columns of tiny wells which are capable of holding a few milliliters of the solvent in which the reaction will occur, is utilized. It is possible to then use n variants of reactant A, and m variants of reactant B, to obtain n x m variants, in n x m wells. One of ordinary skill in the art will realize that this particular procedure is most useful when smaller libraries are desired, and the specific wells can provide a ready means to identify the library members in a particular well.

In another embodiment of the present invention, a solid phase synthesis technique is utilized, in which the desired scaffold structures are attached to the solid phase directly or though a linking unit, as discussed above. Advantages of solid phase techniques include the ability to more easily conduct multi-step reactions and the ability to drive reactions to completion because excess reagents can be utilized and the unreacted reagent washed away. Perhaps one of the most significant advantages of solid phase synthesis is the ability to use a technique called "split and pool", in addition to the parallel synthesis technique, developed by Furka. (Furka et al., *Abstr. 14th Int. Congr. Biochem.*, Prague, Czechoslovakia, 1988, 5, 47; Furka et al., *Int. J Pept. Protein Res.* 1991, 37, 487; Sebestyen et al., *Bioorg. Med. Chem. Lett.*, 1993, 3, 413.) In this technique, a mixture of related compounds can be made in the same reaction vessel, thus substantially reducing the number of containers required for the synthesis of very large libraries, such as those containing as many as or more than one million library members. As an example, the solid support scaffolds can be divided into n vessels, where n represents the number species of reagent A to be reacted with the scaffold structures. After reaction, the contents from n vessels are combined and then split into m vessels, where m represents the number of species of reagent B to be reacted with the scaffold structures. This procedure is repeated until the desired number of reagents is reacted with the scaffold structures to yield the inventive library.

The use of solid phase techniques in the present invention may also include the use of a specific encoding technique. Specific encoding techniques have been reviewed by Czarnik. (Czarnik, A. W., *Current Opinion in Chemical Biology*, 1997, 1, 60.) As used in the present invention, an encoding technique involves the use of a particular "identifying agent" attached to the solid support, which enables the determination of the structure of a specific library member without reference to its spatial coordinates. One of ordinary skill in the art will also realize that if smaller solid phase libraries are generated in specific reaction wells, such as 96 well plates, or on plastic pins, the reaction history of these library members may also be identified by their spatial coordinates in the particular plate, and thus are spatially encoded. It is most preferred, however for large combinatorial libraries, to use an alternative encoding technique to record the specific reaction history.

Examples of alternative encoding techniques that can be utilized in the present invention include, but are not limited to, spatial encoding techniques, graphical encoding techniques, including the "tea bag" method, chemical encoding methods, and spectrophotometric encoding methods. Spatial encoding refers to recording a reaction's history based on its location. Graphical encoding techniques involve the coding of each synthesis platform to permit the generation of a relational database. Examples of preferred spectrophotometric encoding methods include the use of mass spectroscopy, fluorescence emission, and nuclear magnetic resonance spectroscopy. In a preferred embodiment, chemical encoding methods are utilized, which uses the structure of the reaction product to code for its identity. Decoding using this method can be performed on the solid phase or off of the solid phase. One of ordinary skill in the art will realize that the particular encoding method to be used in the present invention must be selected based upon the number of library members desired, and the reaction chemistry employed.

Subsequent characterization of the library members, or individual compounds, can be performed using standard analytical techniques, such as mass spectrometry, Nuclear Magnetic Resonance Spectroscopy, and gas chromatography.

Once specific libraries of compounds have been prepared, specific assay techniques, such as those described herein, may be utilized to test the ability of compounds to inhibit the osteoclast proton pump. In certain preferred embodiments, high throughput assay techniques are utilized.

Uses of Compounds of the Invention

As discussed above, the compounds of the present invention are useful in the selective treatment and/or prevention of metabolic bone disorders. In certain preferred embodiments, these compounds are useful for the treatment of diseases and conditions associated with osteoclast overactivity. In still other preferred embodiments, the compounds of the present invention are selective inhibitors of the osteoclast proton pump and thus inhibit bone resorption.

The present invention therefore provides a method for the treatment and/or porphylaxis of diseases associated with over activity of osteoclasts in mammals which method comprises the administration of an effective non-toxic amount of a selective inhibitor of mammalian osteoclasts, or a pharmaceutically composition thereof.

In a further aspect, the present invention provides an inhibitor of mammalian osteoclasts, for example any one of the compounds of the present invention or a pharmaceutical composition thereof. In particular, the method of present invention comprises providing any one of the compounds of the present invention or a pharmaceutically composition thereof, for use in the treatment of and/or prophylaxis of osteoporosis and related osteopenic diseases.

It will be appreciated that, in addition to the treatment or prevention of osteoporosis, particularly osteoporosis associated with the peri and post menopausal conditions, the present invention also contemplates the treatment and prophylaxis of Paget's disease, hypercalcemia associated with bone neoplasms and other types of osteoporotic diseases and related disorders, including but not limited to involutional osteoporosis, Type I or postmenopausal osteoporosis, Type II or senile osteoporosis, juvenile osteoporosis, idiopathic osteoporosis, endocrine abnormality, hyperthyroidism, hypogonadism, ovarian agensis or Turner's syndrome, hyperadrenocorticism or Cushing's syndrome, hyperparathyroidism, bone marrow abnormalities, multiple myeloma and related disorders, systemic mastocytosis, disseminated carcinoma, Gaucher's disease, connective tissue abnormalities, osteogenesis imperfecta, homocystinuria, Ehlers-Danlos syndrome, Marfan's syndrome, Menke's syndrome, immobilization or weightlessness, Sudeck's atrophy, chronic obstructive pulmonary disease, chronic heparin administration, and chronic ingestion of anticonvulsant drugs In addition, the present invention encompasses the use of the inventive compounds and pharmaceutical compositions for the treatment and prophylaxis of diseases that respond to the inhibition of the osteoclast proton pump and/or are associated with bone resorption. For example, the compounds and pharmaceutical compositions may be used to treat other disorders including, but not limited to, rheumatoid arthritis, peridontal disease, periprosthetic osteolysis, other autoimmune diseases, neoplastic destruction of the bone, and cancer. It will also be appreciated that the treatment of other disorders and/or secondary conditions resulting from overactivity of osteoclasts that are not specifically listed herein, is also contemplated by the method of the present invention.

Therapeutic/Prophylactic Administration and Pharmceutical Compositions

When the compounds of the present invention are used for therapeutic and/or prophylactic administration, they can exist in free form, or, where appropriate, in salt form. Pharmceutically acceptable salts of many types of compounds and their preparation are well-known to those of skill in the art. The pharmaceutically acceptable salts of compounds of this invention include the conventional non-toxic salts or the quaternary ammonium salts of such compounds which are formed, for example, from inorganic or organic acids of bases.

The compounds of the invention may form hydrates or solvates. It is known to those of skill in the art that charged compounds form hydrated species when lyophilized with water, or form solvated species when concentrated in solution with an appropriate organic solvent.

This invention relates to pharmaceutical compositions comprising a therpeutically (or prophylactically) effective amount of the compound, and a pharmaceutically acceptable carrier or excipient. Carriers include, e.g., saline, buffered saline, dextrose, water, glycerol, ethanol, and combinations thereof, and are discussed in greater detail below. The composition, if desired, can also contain minor amounts of wetting or emulsifying agents, or pH buffering agents. The composition can be a liquid solution, suspension, emulsion, tablet, pill, capsule, sustained release formulation, or powder. The compsition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation.

The pharmaceutical carrier may be, for example, either a solid or liquid.

Illustrative solid carriers include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidannts, compression aids, binders or tablet-disintegrating agents; it can also be an encapsulating material. In powders the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, et. Liquid carriers are used in preparing solutions, suspensions, emulsions, syrups, elixirs and pressurized compositions. The active ingredient can be dissolved or suspended in a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carrier for pressurized compositions can be halogenated hydrocarbon or other pharmaceutically propellant. Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The carrier or excipient may include time delay material well known to the art, such as glyceryl monostearate or glyceryl distearate along or with a wax, ethylcellulose, hydroxypropylmethylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) has been recognized as providing an acceptable oral formulation for other compounds, and may be adapted to formulations for various compounds of this invention.

A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of the compound may be dissolved in an aqueous solution or an organic or inorganic acid, such as a 0.3 M solution of succinic acid or citric acid. Alternatively, acidic derivatives can be dissolved in suitable basic solutions. If a soluble salt form is not available, the compound is dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0–60% of the total volume.

Various delivery systems are know and can be used to administer the compound, or the various formulations thereof, including tablets, capsules, injectable solutions, encapsulation in liposomes, microparticles, microcapsules, etc. Methods of introduction include but are not limited to dermal, intradermal, intramuscular, intraperitoneal, intravenous, subcutaneous, intranasal, pulmonary, epidural, ocular and (as is usually preferred) oral routes. The compound may be administered by any convenient or otherwise appropriate route, for example by infusion or bolus injection, by absorption through epithelial or mucocutaneous linings (e.g. oral mucosa, rectal and intestinal mucosa, etc.) and may be administered together with other biologically active agents. Administration can be systemic or local. For treatment or prophylaxis of nasal, bronchial or pulmonary conditions, preferred routes are oral, nasal or via a bronchial aerosol or nebulizer.

In certain embodiments, it may desirable to administer the compound locally to an area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantitity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the compound can also be accomplished topically by administering the compound(s) directly to the affected area of the skin of the individual. For this purpose, the compound is administered or applied in a composition including a pharmacologically acceptable carrier, such as a gel, an ointment, a lotion, or a cream, which includes, without limitation, such carriers as water, glycerol, alcohol, propylene glycol, fatty acids, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

In addition, in certain instances, it is expected that the compound may be disposed witin devices placed upon, in, or under the skin. Such devices include patches, implants, and injections which release the compound into the skin, by either passive or active release mechanisms.

Materials and methods for producing the various formulations are well known in the art and may be adapted for practicing the subject invention. See e.g. U.S. Pat. Nos. 5,182,293 and 4,837,311 (tablets, capsules and other formulations as well as intravenous formulations) and European Patent Application Publication Nos. 0 649 659 (published Apr. 6, 1995; illustrative formulation for IV administration)

and 0 648 494 (published Apr. 19, 1995; illustrative formulation for oral administration).

The effective dose of the compound will typically be in the range of about 0.01 to about 50 mg/kg, preferably about 0.1 to about 10 mg/kg of body weight, administered in single or multiple doses. Generally, the compound may be administered to a subject in need of such treatment in a daily dose range of about 1 to about 2000 mg per subject.

The amount of compound which will be effective in the treatment or prevention of a particular disorder or condition will depend in part on the nature and severity of the disorder or condition, which can be determined by standard clinical techniques. In addition, in vitro or in vivo assays may optionally be employed to help identify optimal dose ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies.

Treatment Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical products, which notice reflects approval by the agency of manufacture, use or sale for human administration.

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the bone targeted dosages, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance which can be adapted to the practice of this invention in its various embodiments and the equivalents thereof.

Exemplification

Compounds of the Invention:

Certain preferred compounds of the present invention include, but are not limited to, those as depicted in Scheme 2:

Scheme 2

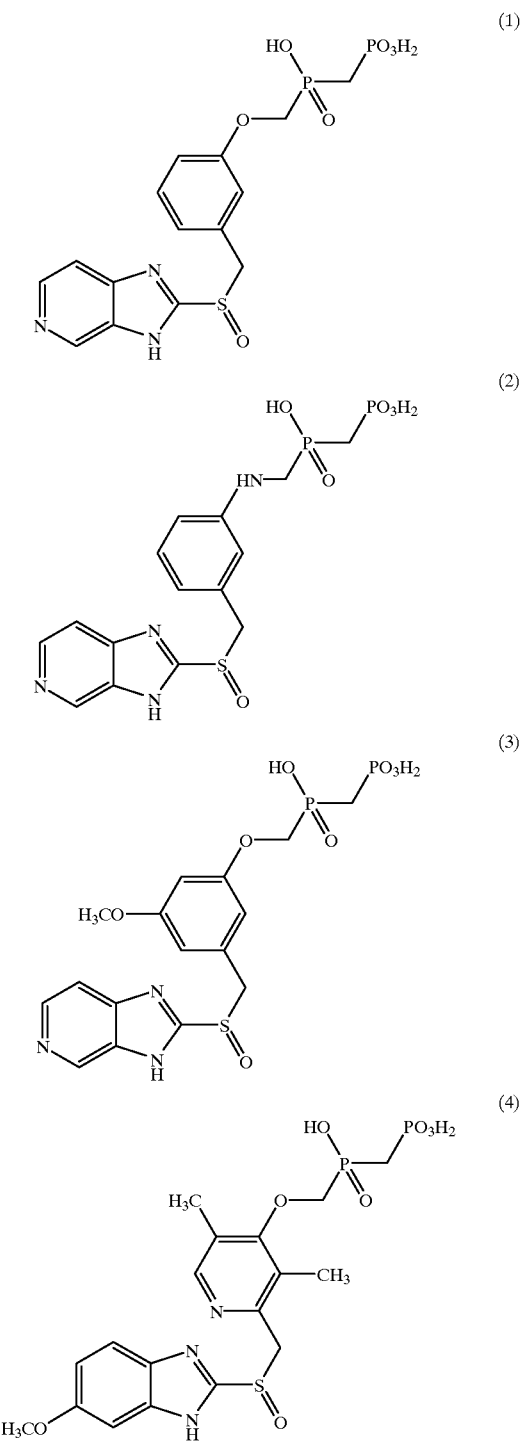

It will be appreciated that for each of the compounds shown above (1)–(4), alternative bone targeting moieties may be used and the compounds may additionally have substituted pyridyl and/or phenyl moieties, as desired. Scheme 3 below depicts a preferred synthesis for compound (1).

Biological Assays:

As discussed above, it is known that specific inhibitors of ATPases are able to inhibit bone resorption in osteoclast cultures. In order to assess the ability of particular compounds to inhibit bone resorption, both in vitro and in vivo

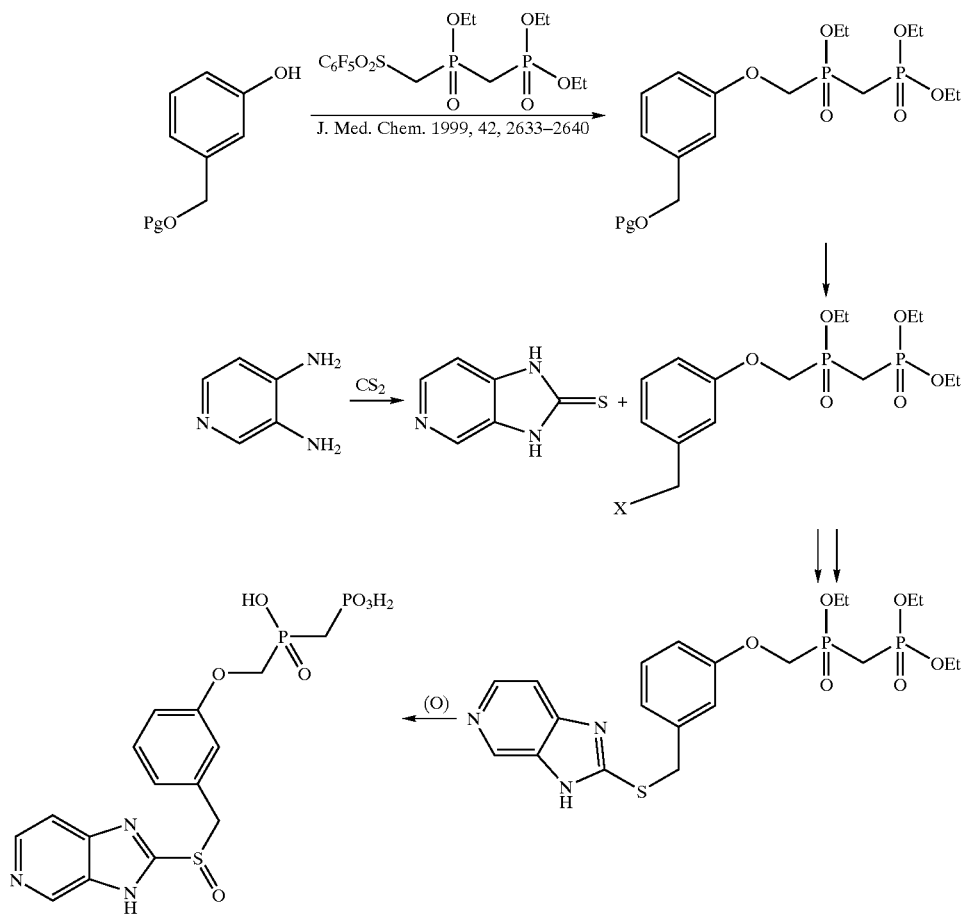

Still other preferred compounds include, but are not limited to, those as depicted in Scheme 4.

assays may be utilized. Examples of preferred assays are described below.

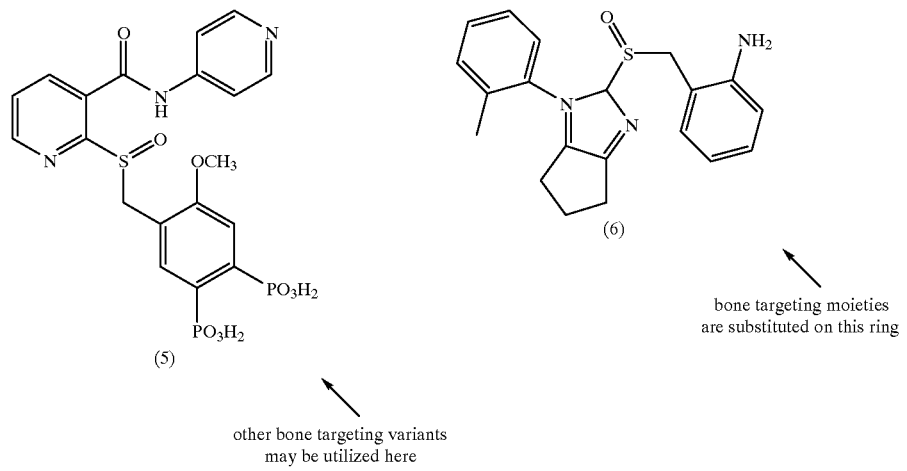

1. Anti-Resorption Cell Assay (Rabbit Osteoclast):

Femurs, tibias, and scapulas were isolated from 3–4 day old New Zealand white rabbits (Millbrook Farms, Amherst, Mass.). Bones were chopped and minced in a-MEM (Gibco-BRL) containing 0.55 g/L $NaHCO_3$, 10 mM HEPES (Gibco-BRL), 50 units/ml penicillin, and 0.05 mg/ml streptomycin, pH 7.1. Bone fragments were allowed to settle by gravitation, supernatant was collected and centrifuged at 400 RPM (Beckman GS-6KR) for two minutes, and the cell pellet was resuspended in the same medium supplemented with 10% HIFBS (Hyclone). For prebinding experiments, 0.75 ml of cell suspension was added to wells containing sperm whale dentine discs preincubated for 2 hours with 0.75 ml culture medium containing a 2× concentration of test compound. Alternatively, 0.75 ml of cell suspension was added to each well containing dentine slices preincubated with 0.75 ml culture medium alone and test compound was added after the adhesion phase. Sperm whale dentine was cut as 1 mm×6 mm circular discs. The adhesion phase was carried out for 30 minutes at 37° C. and 5% $CO_2$ and then the medium and non-adherent cells and debris were removed by aspiration. Fresh culture medium containing serially diluted test compounds was added and cells were incubated on dentine for 24 hours at 37° C. and 5% $CO_2$. After the resorption phase, dentine slices were soaked for 30 seconds in 0.5% sodium hypochlorite, wiped clean of adherent cells, and then stained for 30–45 seconds with 1% toluidine blue. Resorption was measured using reflective light microscopy and automated image analysis. The resorbed area was measured on the entire 6 mm disc. Remaining cells in the 24-well plates were stained for tartrate resistant acid phosphatase (TRAP) and also assessed visually for the presence of fibroblasts. Experiments were carried out containing triplicate samples for each concentration of compound tested with five untreated control samples per plate. $IC_{50}$ values were calculated based on the % resorption in the presence of compound relative to vehicle alone treated control samples. Data were calculated from at least three independent experiments each containing triplicate samples.

2. Hydroxyapatite Assay:

Hydroxyapatite is the principal mineral component of bone. Hydroxyapatite adsorption chromatography is used as an assay to evaluate the bone-targeting potential of both individual bone-targeting moieties ("monomers") and of pharmaceuticals incorporating bone-targeting groups.

Method:

The rentention time of a test compound is measured using a linear gradient from 10 mM sodium phosphate, 0.15 N NaCl, pH=6.8 to 500 mM sodium phosphate, 0.15 N NaCl, pH=-6.8 on a TSK-Gel HA 1000 high pressure liquid chromatography column (7.5 mm×75 mm). The rentention time of the compound is expressed in terms of K=(retention time-void time)/void. This K value is corrected using two reference compounds to correct from inter-column and inter-system variation to obtain a K' value.

Reference Compounds:

K' values were determined for known bone targeted compounds, the bisphosphonate, alendronate and tetracycline. Alendronate gave a K' value of 3.7 and tetracycline gave a K' value of 2.0.

Pro-drugs

As described previously, the compounds of the present invention may be provided as pro-drugs. To give but one example, bone targeting moieities of the following formula:

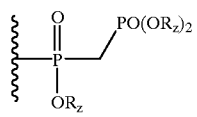

may be protected using the following $R_Z$ groups:

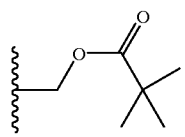

Atack, J. R. et al. J. of Pharmacology and Experimental Therapeutics 1994, 270, 70.

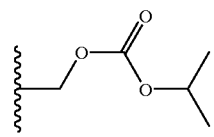

Arimilli, M. N., et al. Antiviral Chemistry & Chemotherapy 1997, 8, 557.

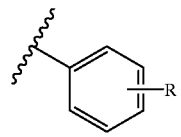

Serafinowska, H. T., et el. J. Med. Chem. 1995, 35, 1372.

Ahlmark, M., J. Med. Chem. 1999, 42, 1473.

Alternatively, the bone targeting moiety may be provided as a pro-drug with the formula:

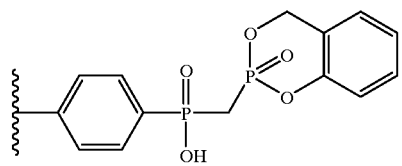

Meier, C., et al. J. Med. Chem. 1998, 41, 1417.

For a review of pro-drugs such as these, please see Krise, J. P., Stella, V. J. *Advanced Drug Delivery Reviews* 1996, 19:287; incorporated herein by reference.

We claim:
1. A compound of formula (I):
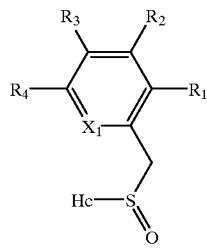
(I)
wherein $X_1$ is CH;
wherein $R_1$, $R_2$, $R_3$, and $R_4$ are each independently hydrogen, lower alkyl, halogen, hydroxy, alkyloxy, aryl, aryloxy, heteroaryl, trifluoromethoxy, cyano, nitro, thio, alkylthio or a bone targeting moiety, wherein said bone targeting moiety is selected from:
i
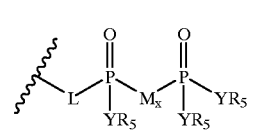
ii
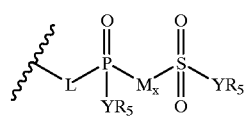
iii
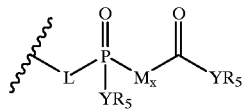
iv
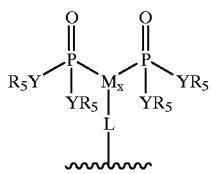
v
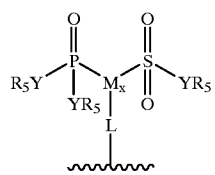
vi
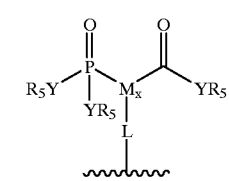
vii
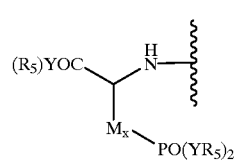
viii
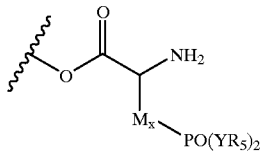
ix
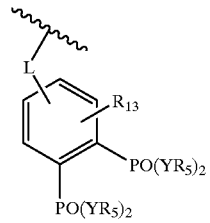
x
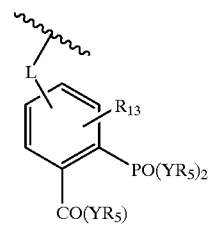
xi
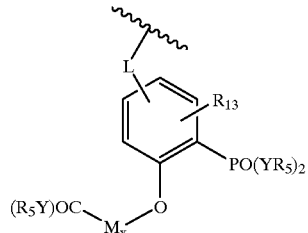
xii
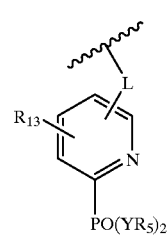
xiii
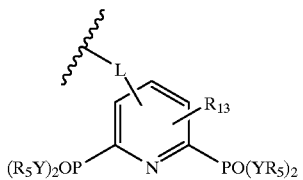
xiv
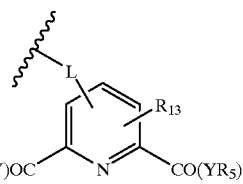

xv

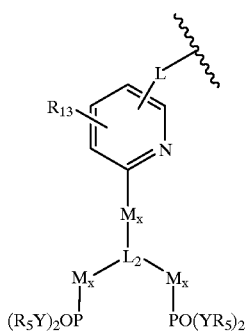

xvi

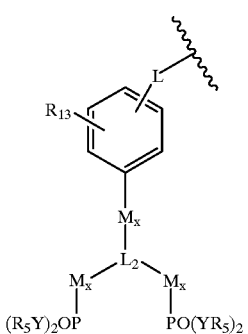

xvii

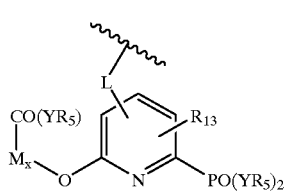

xviii

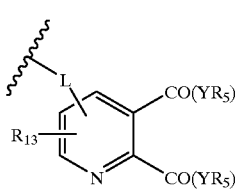

xix

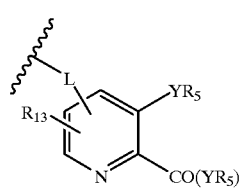

xx

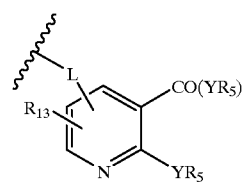

wherein each occurence of M is independently $CV_2$, —NV—, —O— or —S—, wherein each occurrence of V is independently hydrogen, OH, halogen, or aliphatic;

each occurrence of Y is independently a covalent bond, —O—, —S— or $N(R_j)_2$, wherein $R_j$, for each occurrence, is independently hydrogen, aliphatic, heteroaliphatic, aryl, heteroaryl, alkylaryl, or alkylheteroaryl;

each occurrence of x is independently 0–6, and for compounds i-vi, xi, and xvii, x may preferably be 1–6;

wherein L is —$(CH_2)_p$—He—$(CH_2)_n$—, wherein He is absent or is NR', O or S, wherein R' is hydrogen or lower alkyl, n is 0–5, and p is 0–5, except when He is absent, the sum of n and p is 1–5;

wherein $L_2$ is N or $CR_K$, wherein $R_k$ is hydrogen, aliphatic, heteroaliphatic, aryl, heteroaryl, alkylaryl, or alkylheteroaryl;

wherein each occurrence of $R_5$ id independently hydrogen or lower alkyl, with the proviso that if either of $R_2$ or $R_4$ are bone targeting moieties, He, for the bone targeting moiety at $R_2$ or $R_4$, is NR', O, or S, wherein R' is hydrogen or lower alkyl;

wherein $R_{13}$ represents 0–3 substituents selected from hydrogen, halogen, lower alkyl, lower alkenyl, aryl, heteroaryl, carbonyl, thiocarbonyl, ketone, aldehyde, amino, acylamino, amido, amidino, cyano, nitro, azido, sulfonyl, sulfoxido, sulfate, sulfonate, sulfamoyl, sulfonamido, phosphoryl, phosphorothioate, phosphonate, phosphinate, —$(CH_2)_t$-alkyl-, —$(CH_2)_t$ alkenyl-, $(CH_2)_t$alkynyl-, —$(CH_2)_t$aryl-, —$(CH_2)_t$ aralkyl-, —$(CH_2)_t$OH—, —$(CH_2)_t$O-lower alkyl-, $(CH_2)_t$)-lower alkenyl, —$O(CH_2)_tR$, —$(CH_2)_t$S-lower alkyl, —$(CH_2)_t$S-lower alkenyl, —$S(CH_2)_tR$, —$(CH_2)_t$ $NR_2$, —$(CH_2)_t$NR-lower alkyl, —$(CH_2)_t$NR-lower alkenyl, —$NR(CH_2)_tR$, or protected forms of the above, and wherein t is 1–10;

wherein He is:

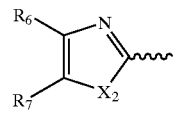

wherein $R_6$ and $R_7$ are each independently selected form the group consisting of bone targeting moiety as described above, hydrogen, lower alkyl, substituted or unsubstituted aryl, and substituted or unsubstituted heteroaryl; or wherein $R_6$ and $R_7$ taken together, comprise a substituted or unsubstituted aryl, heteroaryl, or cycloalkyl moiety, wherein said substituted or unsubstituted aryl, heteroaryl, or cycloalkyl moiety is a single ring or is polycyclic;

wherein $X_2$ comprises $NR_8$ or S, wherein $R_8$ is hydrogen, lower alkyl, substituted or unsubstitued aryl, or substituted or unsubstituted heteroaryl; and whereby at least one of $R_1$–$R_4$, $R_6$, or $R_7$ is substituted with a bone targeting moiety.

2. The compound of claim 1, wherein $R_6$ and $R_7$ taken together comprise a substituted or unsubstituted aryl, heteroaryl, or cycloalkyl moiety, and wherein said aryl, heteroaryl, or cycloalkyl moiety is a single or polycylic ring.

3. The compound of claim 2, wherein said single or polycyclic ring is substituted with methyl or alkoxy.

4. The compound of claim 1, wherein the bone targeting moiety comprises formula (II)

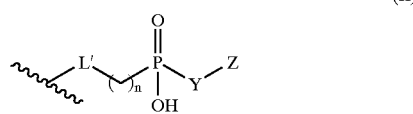
(II)

wherein n is 0–5; wherein L' is —$(CH_2)_p$—He—, wherein He is absent or is NR', O or S, wherein R' is hydrogen or lower alkyl, and p is 0–5, except when He is absent, the sum or n and p is 1–5, with the proviso that if either of $R_2$ or $R_4$ are bone targeting moieties, He, for the bone targeting moiety at $R_2$ or $R_4$, is NR', O or S, wherein R' is hydrogen or lower alkyl; wherein Y is $(CH_2)_q$, wherein q is 1–3, or NH; and wherein Z is $PO(OR_{14})_2$, $SO_2OR_{14}$, or $COOR_{14}$, wherein each occurrence of $R_{14}$ is independently hydrogen or lower alkyl.

5. The compound of claim 4, wherein $R_1$, $R_3$ and $R_4$ are each hydrogen; wherein $R_2$ is a bone targeting moiety, wherein p is O and He is either NR', wherein R' is hydrogen or lower alkyl, or O; wherein He is

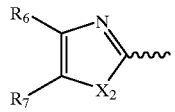

wherein $X_2$ is NH; and $R_6$ and $R_7$ taken together comprise a pyridyl group; wherein Y is $CH_2$ or NH; and wherein Z is $PO(OR_{14})_2$, wherein $R_{14}$ is hydrogen or lower alkyl.

6. The compound of claim 4, wherein $R_1$ and $R_3$ are each hydrogen; wherein $R_4$ is alkoxy; wherein $R_2$ is a bone targeting group; wherein p is O and He is NR', wherein R' is hydrogen or lower alkyl, or O; wherein He is

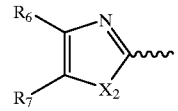

wherein $X_2$ is NH; $R_6$ and $R_7$ taken together comprise a pyridyl group; Y is $CH_2$ or NH; and wherein Z is $PO(OR_{14})_2$, and $R_{14}$ is hydrogen or lower alkyl.

7. A pharmaceutical composition comprising:
   a compound of any one of claims 1, 2, 3, 4, 5, or 6; and
   a pharmaceutically acceptable carrier or excipient.

8. A method for the prevention or treatment of a disease or secondary condition associated with overactivity of osteoclasts in a subject which method comprises the administration of an effective amount of a compound of claims 1–6 or the composition fo claim 7 to a subject in need thereof.

9. The method of claim 8, wherein said disease or secondary condition is selected from the group consisting of osteoporosis, Paget's Diesease, hypercalcemia, rheumatoid arthritis, metastatic bone destruction, cancer, and immune disorder.

* * * * *